United States Patent [19]
Yamaki et al.

[11] Patent Number: 5,858,012
[45] Date of Patent: Jan. 12, 1999

[54] PULL-ON DISPOSABLE DIAPER

[75] Inventors: Rumi Yamaki; Kenichi Hisada, both of Ehime-ken, Japan

[73] Assignee: Uni-Charm Corporation, Ehime-ken, Japan

[21] Appl. No.: 965,613

[22] Filed: Nov. 6, 1997

[30] Foreign Application Priority Data

Nov. 6, 1996 [JP] Japan .................................. 8-294096

[51] Int. Cl.⁶ .................................................. A61F 13/15
[52] U.S. Cl. ...................................... 604/385.2; 604/358
[58] Field of Search ............................... 604/358, 385.1, 604/385.2

[56] References Cited

U.S. PATENT DOCUMENTS

Re. 35,687  12/1997  Igaue et al. ........................ 604/385.2
5,415,649   5/1995   Watanabe et al. .................. 604/385.2
5,449,353   9/1995   Watanabe et al. .................. 604/385.2

*Primary Examiner*—Aaron J. Lewis
*Assistant Examiner*—Dennis Ruhl
*Attorney, Agent, or Firm*—Lowe Hauptman Gopstein Gilman & Berner

[57] ABSTRACT

A pull-on disposable diaper has front and rear waist regions and a crotch region extending therebetween. A waist-opening of the diaper is provided with elastic members being stretchable circumferentially of the waist-opening. An absorbent core has a front end lying below the elastic members and a rear end extending above the elastic members.

4 Claims, 3 Drawing Sheets

PULL-ON DISPOSABLE DIAPER

BACKGROUND OF THE INVENTION

This invention relates generally to pull-on disposable diapers and the like.

Pull-on disposable diapers are well known. To improve fit, the waist-opening and leg-openings of such diaper have been provided with stretched elastic members bonded thereto in the proximity of their peripheral edges. A body fluid absorbent core of the diaper is disposed between a liquid-permeable sheet and a liquid-impermeable sheet so as to extend across a crotch region of the diaper from a front waist region into a rear waist region thereof. Longitudinally opposite ends of the absorbent core lying in the front and rear waist regions of the diaper, respectively, underlie the elastic members associated with the waist-opening.

The pull-on diaper is apt to slip down during use. While it is possible to pull up the pull-on diaper by holding an edge of the waist-opening, even such a simple operation is often difficult for the elderly and the sick. Although it is often relatively easy to pull up a front side of the diaper, it is often difficult for the elderly and sick to hold a rear side of the diaper with his or her hands and thereby pull up the rear side. In such a case, the wearer's hips might be left exposed.

SUMMARY OF THE INVENTION

In view of the problem as described above, it is a principal object of the invention to provide a diaper so improved that unintentional exposure of the wearer's hip can be minimized even if the diaper more or less slips down.

The object set forth above is achieved, according to the invention, by a pull-on disposable diaper comprising an absorbent including a liquid-permeable topsheet, a liquid-impermeable backsheet and an absorbent core disposed therebetween, the diaper thereby having a front waist region, a rear waist region and a crotch region extending therebetween. A waist-opening and a pair of leg-openings defined by the respective regions and are provided with elastic members which are stretchable circumferentially of the respective openings and bonded in stretched conditions thereto. The disposable diaper is characterized in that the elastic members associated with the waist-opening extend across said front and rear waist regions substantially at the same vertical level of the diaper; and the absorbent core has a front end in the front waist region and a rear end in the rear waist region. The front end lies below the elastic members associated with the waist-opening and the absorbent core extends, in the rear waist region, upward beyond said elastic members associated with the waist-opening so that the absorbent core has a rear end lying above said elastic members associated with the waist-opening.

The pull-on disposable diaper according to the invention minimizes unintentional exposure of the wearer's hip since a depth of the rear waist region down to the crotch region is dimensioned to be significantly larger than that of the front waist region.

Other and further objects, features and advantages of the invention will appear more fully from the following description.

DESCRIPTION OF THE PREFERRED EMBODIMENTS

Figure 1:
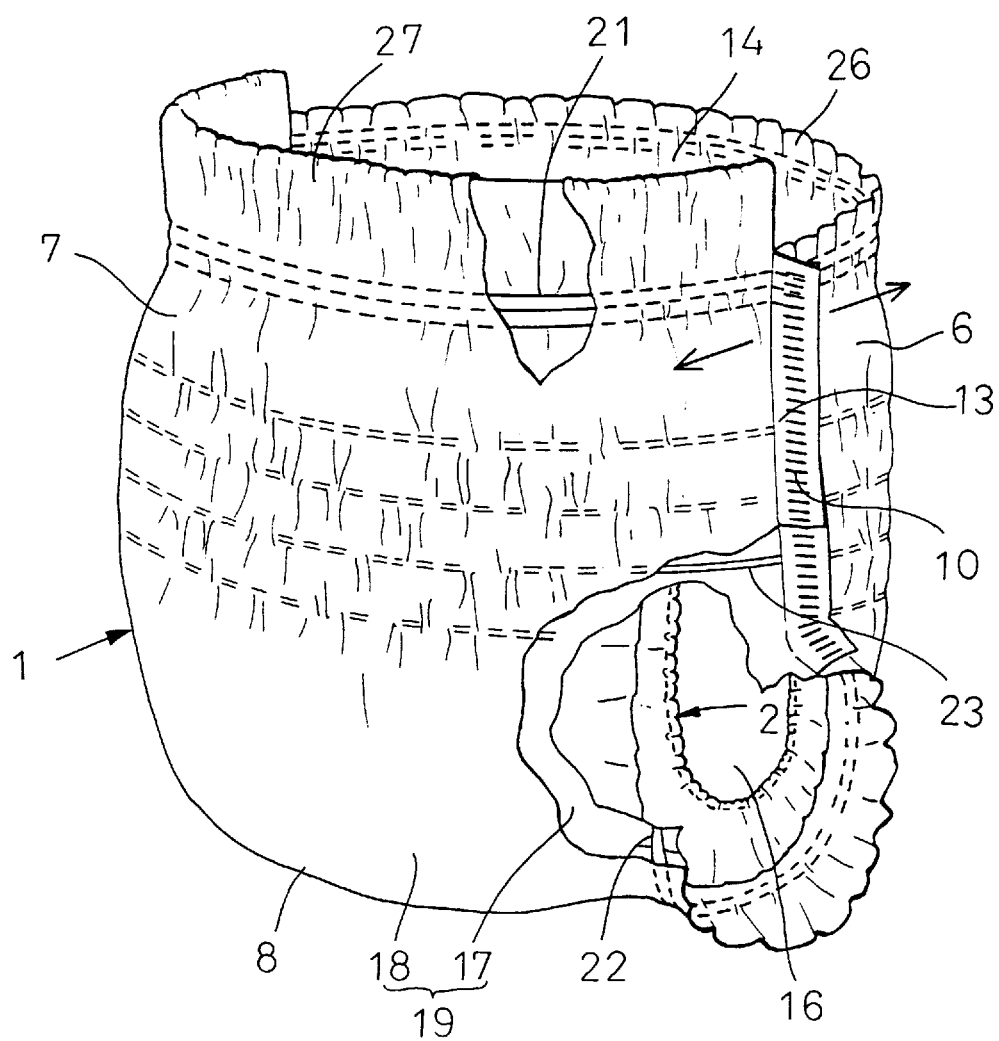
FIG. 1 is a perspective view showing an embodiment of a pull-on diaper according to the invention as partially broken away.

A pull-on or shorts type disposable diaper shown by FIG. 1 in a perspective view as partially broken away basically comprises a supporter 1 in the form of shorts and an absorbent 2. The supporter 1 is composed of a front waist region 6, a rear waist region 7 and a crotch region 8 extending between the front and rear waist regions 6, 7. These front and rear waist regions 6, 7 are put flat and bonded together along their transversely opposite side edges at vertically intermittent spots 10 so as to form right and left closed side edges 13 of the waist regions, a waist-opening 14 and a pair of leg-openings 16. The supporter 1 is made of a laminated sheet 19 comprising a liquid-impermeable plastic film serving as a topsheet 17 and an air-permeable spun-bond nonwoven fabric serving as a backsheet 18. The waist-opening 14 and the leg-openings 16 are respectively provided in the proximity of their peripheral edges with a plurality of elastic members 21, 22 which are stretchable circumferentially of their openings, respectively. These elastic members 21, 22 each have a width of 0.5~3 mm and are laid between the topsheet 17 and the backsheet 18 and bonded in their stretched condition to an inner surface of at least one of the topsheet 17 and the backsheet 18. Referring to FIG. 1, the elastic members 21 associated with the front and rear waist regions 6, 7 extend across these waist regions 6, 7 substantially at the same level above the bottom of the crotch region 8. Below the elastic members 21, the front and rear waist regions 6, 7 are additionally provided with a plurality of second elastic members 23. These second elastic members 23 each have a relatively large width of 3~10 mm and are stretchable circumferentially of the waist regions and bonded in their stretched conditions to an inner surface of at least one of the topsheet 17 and the backsheet 18. As shown, an upper end 27 of the rear waist region 7 sufficiently extends upward beyond the elastic members 21 to overlie an upper end 26 of the front waist region 6.

Figure 2:
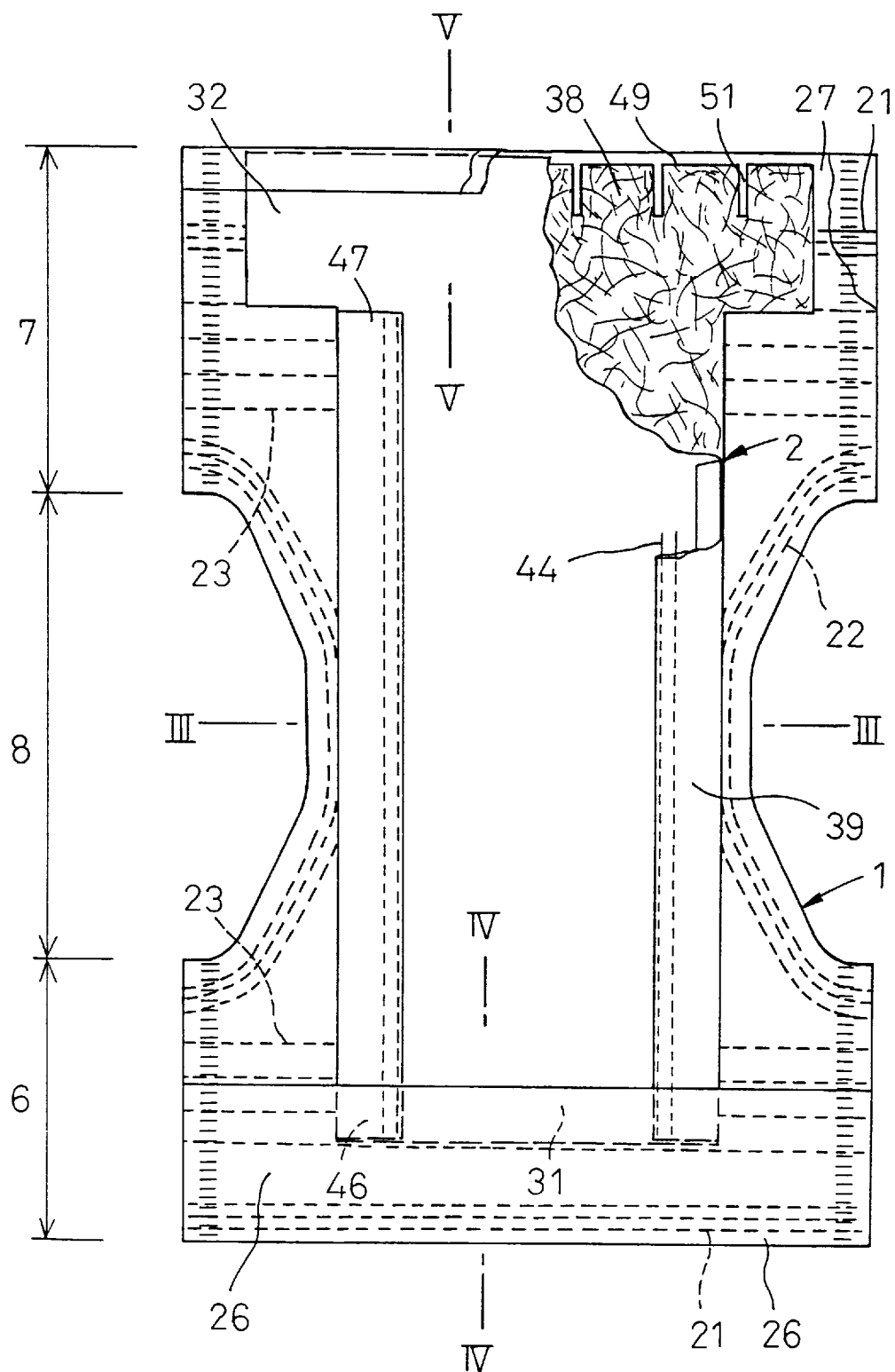
FIG. 2 is a plan view showing the diaper unfolded back and forth from its state shown in FIG. 1, as partially broken away.
Figure 3:
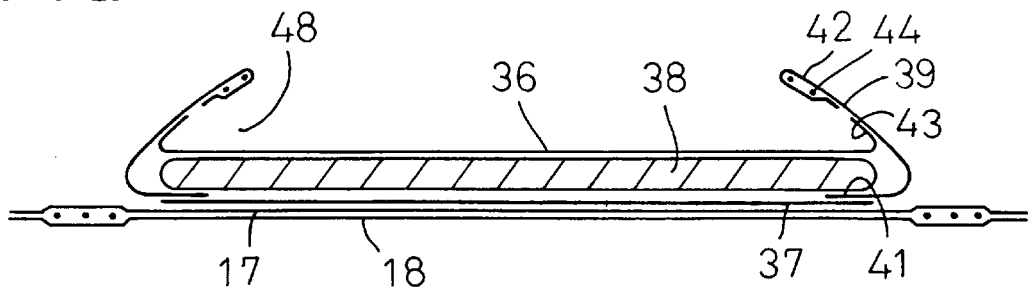
FIG. 3 is a sectional view taken along a line III—III in FIG. 2.

FIG. 2 is a plan view showing, as partially broken away, the diaper having the front and rear waist regions 6, 7 cut apart along the side edges 13 and longitudinally unfolded from the state shown in FIG. 1. FIG. 3 is a sectional view taken along a line III—III in FIG. 2 which divides the diaper in two longitudinally. As will be apparent from FIG. 2, the supporter 1 is substantially hourglass-shaped while the absorbent 2 is T-shaped and extends across the front and rear waist region 6, 7 and the crotch region 8 of the supporter 1. A front end 31 of the absorbent 2 extends in the front waist region 6 of the supporter 1 and terminates inwardly of the elastic members 21. A rear end 32 of absorbent 2 is transversely enlarged in the rear waist region 7 relative to the front end 31 and extends beyond or outwardly of the elastic members 21.

The absorbent 2 comprises a topsheet 36 made of a liquid-permeable spun-bond nonwoven fabric, a backsheet 37 made of a liquid-impermeable plastic film and a liquidabsorbent core 38 disposed between the topsheet 36 and the backsheet 37 and comprises fluff pulp fibers or a mixture of fluff pulp fibers and super-water-absorptive polymer particles. The backsheet 37 is bonded to the topsheet 17 of the supporter 1 by means of hot melt adhesive (not shown). The absorbent 2 is provided along its transversely opposite side edges extending in the proximity of the crotch region 8 with a pair of barrier cuffs 39 extending longitudinally of the absorbent 2. Each of the barrier cuffs 39 comprises a liquid-impermeable strip extending longitudinally of the diaper, which has one side edge 41 bonded to the backsheet 37 and the other side edge 42 extending in parallel to the side edge 41 and folded inwardly of the diaper. Each side edge 43 of the topsheet 36 is bonded to the barrier cuff 39 along its area defined between the side edges 41, 42. The side edge 42 folded inwardly of the diaper contains an elastic member 44 bonded in its longitudinally extended condition to an inner surface of the folded side edge 42. An inner surface of the barrier cuff 39 is bonded at its longitudinally opposite ends 46, 47 (FIG. 2) to an upper surface of the topsheet 36 by means of hot melt adhesive (not shown). With the diaper being in the state shown by FIG. 1, the elastic member 44 contracts and, in consequence, an intermediate portion of the barrier cuff 39 extending between the longitudinally opposite ends 46, 47 rises on the topsheet 36 so as to define a pocket which opens inwardly of the diaper. The absorbent core 38 has a plurality of parallel notches 51 extending inward (i.e., downward as viewed in FIG. 1) from a rear end 49 and these notches 51 allow the absorbent core 38 to be smoothly curved along the wearer's waist.

Figure 4:
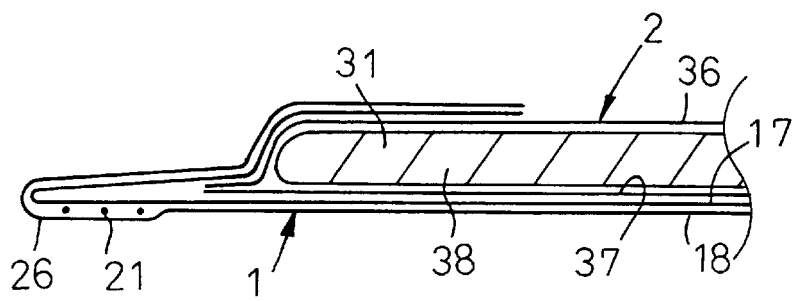
FIG. 4 is a sectional view taken along a line IV—IV in FIG. 2.
Figure 5:
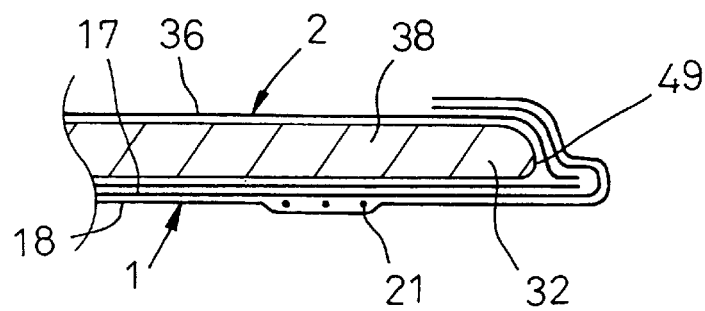
FIG. 5 is a sectional view taken along a line V—V in FIG. 2.

FIGS. 4 and 5 are sectional views taken along lines IV—IV and V—V in FIG. 2, respectively. The topsheet 36 and the backsheet 37 covering the absorbent core 38 are bonded along their portions extending outward beyond a peripheral edge of the absorbent core 38 and placed upon each other. In the front waist region 6, the topsheet 17 and the backsheet 18 of the supporter 1 are folded along the front end 26 of the supporter 1 inwardly of the diaper and partially cover the absorbent 2. The topsheet 17 folded in this manner is bonded to the backsheet 18 folded together with the topsheet 17, on the one hand, and bonded to the topsheet 36 of the absorbent 2, on the other hand (FIG. 4). In the rear waist region 7, the topsheet 17 and the backsheet 18 are folded along the rear end 49 of the absorbent core 38 inwardly of the diaper and bonded to the topsheet 36 (FIG. 5). The arrangement that both the front end 31 and the rear end 32 of the absorbent 2 are covered with the topsheet 17 and the backsheet 18 assures that the wearer is free from an uncomfortable feeling of wetness even if body fluids spread to the front and rear ends 31, 32.

Figure 6:
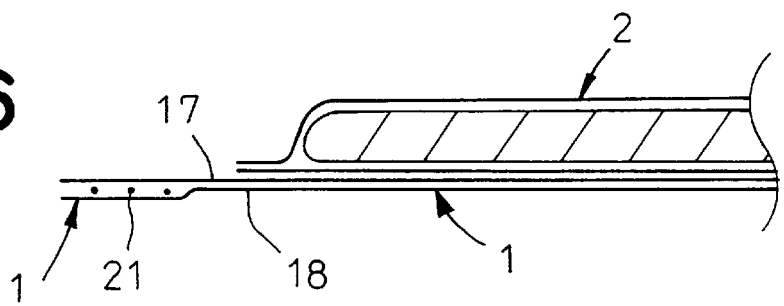
FIG. 6 is a view similar to FIG. 4 illustrating an alternative embodiment of the invention.
Figure 7:
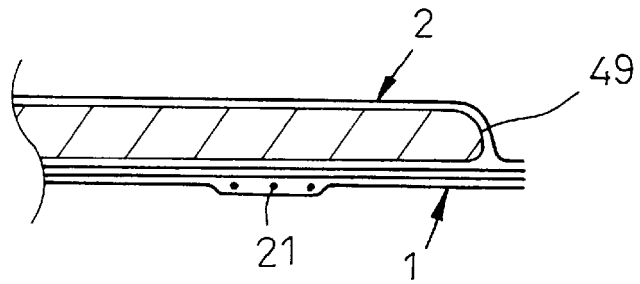
FIG. 7 is a view similar to FIG. 5 illustrating the alternative embodiment of the invention.

FIGS. 6 and 7 are views similar to FIGS. 4 and 5, respectively, showing still another alternative embodiment of the invention. Referring to FIGS. 6 and 7, the topsheet 17 and the backsheet 18 of the supporter 1 extend longitudinally without being folded and the absorbent 2 merely rests on these topsheet 17 and the backsheet 18. Obviously, the absorbent 2 is bonded to the supporter 1 and the absorbent 2 might shift relative to the supporter 1. However, the arrangement illustrated by FIGS. 6 and 7 is simpler than that illustrated by FIGS. 4 and 5 and the manufacturing cost of the diaper can be correspondingly reduced.

It should be understood that the arrangements of the front waist region 6 illustrated by FIGS. 4 and 6 and the arrangements of the rear waist region 7 illustrated by FIGS. 5 and 7 may be selectively combined.

In the diaper configured as described herein above, the topsheet 17 and the backsheet 18 of the supporter 1 are not limited to those illustrated and it is not critical whether they comprise liquid-permeable sheets or liquid-impermeable sheets. The topsheet 36 of the absorbent 2 also is not limited to the liquid-permeable nonwoven fabric and it is possible to replace this by a liquid-permeable plastic film. For implementation of the invention, bonding of various components such as the topsheet 17 and the backsheet 18 of the supporter 1 as well as the topsheet 36 and the backsheet 37 of the absorbent 2 may be achieved not only by use of suitable adhesive such as hot melt adhesive but also by use of the known heat-sealing technique so long as any one or more of these sheets are of heat-sealable nature.

While the invention has been described hereinabove in connection with the pull-on disposable diaper basically comprising the supporter 1 in the form of shorts and the absorbent 2, the invention may be implemented by using the liquid-permeable topsheet 17 and the liquid-impermeable backsheet 18 to form the supporter 1 in the form of shorts and by disposing the T-shaped absorbent core 38 between these two sheets 17, 18.

Having described our invention as related to the embodiment shown in the accompanying drawings, it is our intention that the invention be not limited by any of the details of description, unless otherwise specified, but rather be construed broadly within its spirit and scope as set out in the accompanying.

What is claimed is:

1. A pull-on disposable diaper, comprising an absorbent including a liquid-permeable topsheet, a liquid-impermeable backsheet and an absorbent core disposed therebetween to jointly define a front waist region, a rear waist region and a crotch region extending therebetween, and a waist-opening and a pair of leg-openings defined by said respective regions, wherein said waist-opening and said leg-openings include elastic members being stretchable circumferentially of said respective openings and bonded thereto in a stretched condition thereof; wherein said elastic members associated with said waist-opening extend across said front and rear waist regions substantially at the same level vertically of said diaper; and said absorbent core has a front end in said front waist region and a rear end in said rear waist region, wherein said front end terminates below said elastic members associated with the waist-opening in the front waist regions and said absorbent core includes said rear end that extends, in said rear waist region, upward above said elastic members associated with the waist-opening in the rear waist region.

2. The diaper according to claim 1, further comprising a liquid-impermeable sheet, extending in the rear waist region to cover said rear end.

3. The diaper according to claim 1, wherein said absorbent core rear end has a plurality of notches extending downward in parallel one to another.

4. The diaper according to claim 1, further comprising a shorts-shaped member also having front and rear waist regions and a crotch region therebetween, and wherein said absorbent is bonded to an inner surface of the shorts-shaped member.

* * * * *

(12) EX PARTE REEXAMINATION CERTIFICATE (5834th)
United States Patent
Yamaki et al.

(10) Number: US 5,858,012 C1
(45) Certificate Issued: Jul. 31, 2007

(54) PULL-ON DISPOSABLE DIAPER

(75) Inventors: Rumi Yamaki, Ehime-ken (JP); Kenichi Hisada, Ehime-ken (JP)

(73) Assignee: Uni-Charm Corporation, Kawanoe-Shi, Ehime-Ken (JP)

Reexamination Request:
No. 90/006,974, Mar. 19, 2004

Reexamination Certificate for:
Patent No.: 5,858,012
Issued: Jan. 12, 1999
Appl. No.: 08/965,613
Filed: Nov. 6, 1997

(30) Foreign Application Priority Data
Nov. 6, 1996 (JP) .............................................. 8-294096

(51) Int. Cl.
*A61F 13/15* (2006.01)
*A61F 13/20* (2006.01)

(52) U.S. Cl. .................................... 604/385.27; 604/358

(58) Field of Classification Search ....................... None
See application file for complete search history.

(56) References Cited

U.S. PATENT DOCUMENTS 5,745,922 A * 5/1998 Rajala et al. ................. 2/243.1

FOREIGN PATENT DOCUMENTS

| EP | 0 329 160 | 8/1989 |
|---|---|---|
| EP | 0 450 541 | 10/1991 |
| GB | 2 253 131 | 9/1992 |

* cited by examiner

*Primary Examiner*—Beverly M. Flanagan

(57) ABSTRACT

A pull-on disposable diaper has front and rear waist regions and a crotch region extending therebetween. A waist-opening of the diaper is provided with elastic members being stretchable circumferentially of the waist-opening. An absorbent core has a front end lying below the elastic members and a rear end extending above the elastic members.

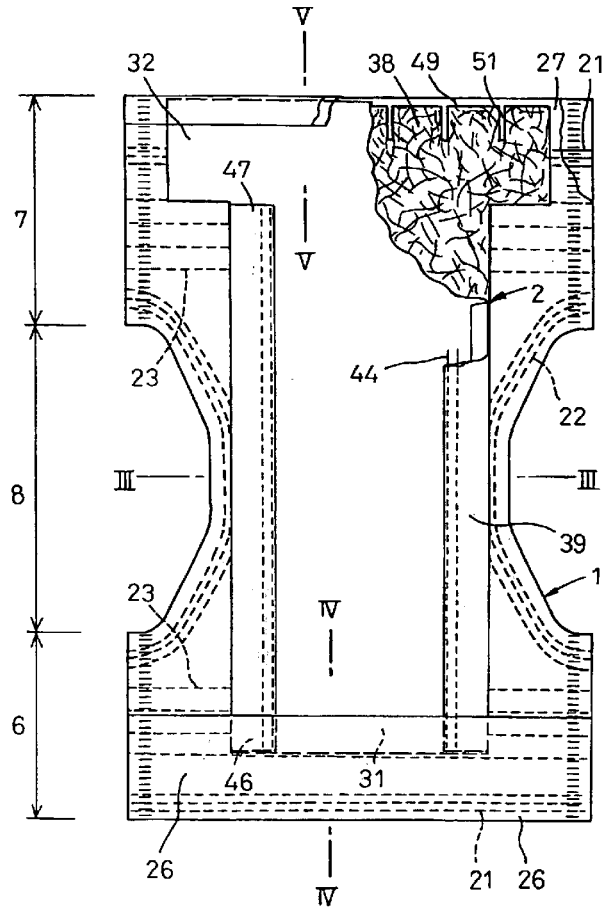

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3 are determined to be patentable as amended.

Claims 2 and 4 dependent on an amended claim, are determined to be patentable.

New claims 5–14 and 15 are added and determined to be patentable.

1. A pull-on disposable diaper, comprising an absorbent including a liquid-permeable topsheet, a liquid-impermeable backsheet and an absorbent core disposed therebetween to jointly define a front waist region, a rear waist region and a crotch region extending therebetween, and a waist-opening and a pair of leg-openings defined by said respective regions, wherein said waist-opening and said leg-openings include elastic members being stretchable circumferentially of said respective openings and bonded thereto in a stretched condition thereof; wherein said elastic members associated with said waist-opening extend across said front and rear waist regions substantially at the same level vertically of said diaper; [and]

said absorbent core has a front end in said front waist region and a rear end in said rear waist region, wherein said front end terminates below said elastic members associated with the waist-opening in the front waist [regions] *region* and said absorbent core includes said rear end that extends, in said rear waist region, upward above said elastic members associated with the waist-opening in the rear waist regions; *and*

*said waist-opening has a front circumferential edge in said front waist region and a rear circumferential edge in said rear waist region, said rear circumferential edge being at a higher level than said front circumferential edge.*

3. [The diaper according to claim 1, wherein] *A pull-on disposable diaper, comprising an absorbent including a liquid-permeable topsheet, a liquid-impermeable backsheet and an absorbent core disposed therebetween to jointly define a front waist region, a rear waist region and a crotch region extending therebetween, and a waist-opening and a pair of leg-openings defined by said respective regions, wherein said waist-opening and said leg-openings include elastic members being stretchable circumferentially of said respective openings and bonded thereto in a stretched condition thereof, wherein*

*said elastic members associated with said waist-opening extend across said front and rear waist regions substantially at the same level vertically of said diaper;*

*said absorbent core has a front end in said front waist region and a rear end in said rear waist region, wherein* said front end terminates below said elastic members associated with the waist-opening in the front waist region and said absorbent core includes said rear end that extends, in said rear waist region, upward above said elastic members associated with the waist-opening in the rear waist region; and said absorbent core rear end has a plurality of notches extending downward in parallel one to another.

5. *The diaper according to claim 1, wherein said absorbent core rear end has a plurality of notches extending downward in parallel one to another.*

6. *The diaper according to claim 1, wherein said backsheet is folded along said front circumferential edge inwardly of the diaper, and at least partially covers the front end of said absorbent core.*

7. *The diaper according to claim 6, wherein said backsheet is folded along said rear circumferential edge inwardly of the diaper, and at least partially covers the rear end of said absorbent core.*

8. *The diaper according to claim 1, wherein said backsheet is folded along said rear circumferential edge inwardly of the diaper, and at least partially covers the rear end of said absorbent core.*

9. *The diaper according to claim 1, wherein said backsheet is folded along at least one of said front and rear circumferential edges inwardly of the diaper, at least partially covers the respective one of said front and rear ends of said absorbent core, and is bonded to the topsheet.*

10. *The diaper according to claim 1, wherein said absorbent core is T-shaped.*

11. *The diaper according to claim 1, wherein a first distance between the rear circumferential edge and a highest one of said elastic members associated with the waist-opening in the rear waist region is greater than a second distance between the front circumferential edge and a highest one of said elastic members associated with the waist-opening in the front waist region.*

12. *The diaper according to claim 11, wherein said backsheet is folded along at least one of said front and rear circumferential edges inwardly of the diaper, and at least partially covers the respective one of said front and rear ends of said absorbent core.*

13. *The diaper according to claim 3, wherein*

*said waist-opening has a front circumferential edge in said front waist region and a rear circumferential edge in said rear waist region; and*

*a first distance between the rear circumferential edge and a highest one of said elastic members associated with the waist-opening in the rear waist region is greater than a second distance between the front circumferential edge and a highest one of said elastic members associated with the waist-opening in the front waist region.*

14. *The diaper according to claim 3, wherein said backsheet is folded along at least one of said front and rear circumferential edges inwardly of the diaper, and at least partially covers the respective one of said front and rear ends of said absorbent core.*

15. *A pull-on disposable diaper, comprising an absorbent including a liquid-permeable topsheet, a liquid-impermeable backsheet and an absorbent core disposed therebetween to jointly define a front waist region, a rear waist region and a crotch region extending therebetween, and a waist-opening and a pair of leg-openings defined by said respective regions, wherein said waist-opening and said leg-openings include elastic members being stretchable circumferentially of said respective openings and bonded thereto in a stretched condition thereof; wherein* said elastic members associated with said waist-opening extend across said front and rear waist regions substantially at the same level vertically of said diaper;

said absorbent core has a front end in said front waist region and a rear end in said rear waist region, wherein said front end terminates below said elastic members associated with the waist-opening in the front waist region and said absorbent core includes said rear end that extends, in said rear waist region, upward above said elastic members associated with the waist-opening in the rear waist region;

said waist-opening has a front circumferential edge in said front waist region and a rear circumferential edge in said rear waist region; and a first distance between the rear circumferential edge and a highest one of said elastic members associated with the waist-opening in the rear waist region is greater than a second distance between the front circumferential edge and a highest one of said elastic members associated with the waist-opening in the front waist region; and said backsheet is folded along at least one of said front and rear circumferential edges inwardly of the diaper, and at least partially covers the respective one of said front and rear ends of said absorbent core.

\* \* \* \* \*